(12) United States Patent
Giroudiere et al.

(10) Patent No.: US 9,174,901 B2
(45) Date of Patent: Nov. 3, 2015

(54) TEMPORARY DESULPHURIZATION REACTOR FOR PRE-TREATING A HYDROCARBON FEED BEFORE STEAM REFORMING WITH A VIEW TO HYDROGEN PRODUCTION

(71) Applicant: IFP Energies nouvelles, Rueil-Malmaison Cedex (FR)

(72) Inventors: Fabrice Giroudiere, Orlienas (FR); Michel Thomas, Lyons (FR); Cedric Nebois, Venissieux (FR)

(73) Assignee: IFP ENERGIES NOUVELLES, Rueil-Malmaison Cedex (FR)

( * ) Notice: Subject to any disclaimer, the term of this patent is extended or adjusted under 35 U.S.C. 154(b) by 376 days.

(21) Appl. No.: 13/848,944

(22) Filed: Mar. 22, 2013

(65) Prior Publication Data
US 2013/0261351 A1 Oct. 3, 2013

(30) Foreign Application Priority Data
Mar. 27, 2012 (FR) ..................................... 12 00911

(51) Int. Cl.
| | | |
|---|---|---|
| C07C 29/76 | (2006.01) | |
| C01B 3/32 | (2006.01) | |
| C01B 3/38 | (2006.01) | |

(52) U.S. Cl.
CPC ................. *C07C 29/76* (2013.01); *C01B 3/323* (2013.01); *C01B 3/38* (2013.01); *C01B 2203/1229* (2013.01); *C01B 2203/1247* (2013.01); *C01B 2203/1258* (2013.01); *C01B 2203/1604* (2013.01)

(58) Field of Classification Search
CPC ...................................................... C07C 29/76
USPC ................................................ 568/917, 913
See application file for complete search history.

(56) References Cited

U.S. PATENT DOCUMENTS

| 6,798,358 | B2 | 9/2004 | Joyce et al. |
| 7,196,639 | B2 | 3/2007 | Joyce et al. |
| 2003/0006913 | A1 | 1/2003 | Joyce et al. |
| 2004/0091753 | A1 | 5/2004 | Terorde et al. |
| 2004/0209602 | A1 | 10/2004 | Joyce et al. |
| 2005/0022449 | A1 | 2/2005 | Katikaneni et al. |
| 2007/0092766 | A1 | 4/2007 | England et al. |
| 2012/0178006 | A1 | 7/2012 | Kani et al. |

FOREIGN PATENT DOCUMENTS

| EP | 1236495 | A1 | 9/2002 |
| EP | 1780256 | A1 | 5/2007 |
| JP | 1275697 | A | 11/1989 |
| JP | 200029001 | A | 10/2000 |
| JP | 2002151124 | A | 5/2002 |
| JP | 200293447 | A | 2/2003 |
| JP | 2004307236 | A | 11/2004 |
| JP | 2006008459 | A | 1/2006 |
| JP | 2006111766 | A | 4/2006 |
| JP | 2007290942 | A | 11/2007 |
| JP | 2009079183 | A | 4/2009 |
| JP | 2009249203 | A | 10/2009 |
| WO | 2011077752 | A1 | 6/2011 |
| WO | 2012169199 | A1 | 12/2012 |

OTHER PUBLICATIONS

International Search Report from related application PCT/JP2010/007520 dated Mar. 1, 2011.
IPRP and Written Opinion from FR1200911 dated Jan. 30, 2013.
English Translation Abstract for JP200029001 dated Oct. 17, 2000.
English Translation Abstract for JP2004307236 dated Nov. 4, 2004.
English Translation Abstract for JP4130603B2 dated Aug. 6, 2008.
English Translation Abstract for JP2007290942A dated Nov. 8, 2007.
English Translation Abstract for JP200293447 dated Feb. 14, 2003.
English Translation Abstract for JP2002151124 dated May 24, 2002.
English Translation Abstract for WO2012169199 dated Dec. 13, 2012.
English Translation Abstract for JP2006008459 dated Jan. 12, 2006.
English Translation Abstract for JP2009079183 dated Apr. 16, 2009.
English Translation Abstract for JP01275697 dated Nov. 6, 1989.
English Translation Abstract for JP2009249203 dated Oct. 29, 2009.
English Translation Abstract for JP2006111766 dated Apr. 27, 2006.

*Primary Examiner* — Elvis O Price
(74) *Attorney, Agent, or Firm* — Millen, White, Zelano, Branigan, P.C.

(57) ABSTRACT

The present invention describes a process for pre-treating a steam reforming feed containing sulphur-containing compounds, using two desulphurization reactors:

- a temporary desulphurization reactor (1010) containing an active adsorbent solid;
- a permanent desulphurization reactor (1003) placed upstream of the steam reforming unit, which contains an adsorbent solid in the passivated state, necessitating a depassivation phase in order to be rendered active;

the temporary desulphurization reactor (1010) being disconnected as soon as the adsorbent solid of the permanent desulphurization reactor (1003) has been activated, and the volume of the temporary desulphurization reactor being in the range 1/20 to 1/200 times the volume of the permanent desulphurization reactor.

7 Claims, 2 Drawing Sheets

TEMPORARY DESULPHURIZATION REACTOR FOR PRE-TREATING A HYDROCARBON FEED BEFORE STEAM REFORMING WITH A VIEW TO HYDROGEN PRODUCTION

FIELD OF THE INVENTION

The present invention describes a reactor which will hereinafter be termed a preparation reactor in the context of a process for the production of hydrogen by steam reforming hydrocarbon feeds, such as gas oil or even denatured ethanol, for example.

Hydrocarbons (of the gasoline or gas oil type, for example) or alcohols (for example bio-ethanol) used to supply units for producing hydrogen by steam reforming (autothermal steam reforming, ATR, followed by steam displacement, for example WGS) generally contain a few ppm of sulphur (typically 10 ppm) which it might be economically viable to remove by means of known processes for adsorption on solids of the metal oxide type, possibly in the partially reduced state.

They may, for example, be solids based on passivated nickel on alumina or silica-alumina (for example the adsorbent solid AxTrap-405 from Axens).

Hydrogen production units, particularly when they are small (typically 100 $Nm^3/h$ of $H_2$ produced) may be located far away from petrochemicals plants, for example in a service station or an isolated building, especially when the hydrogen is used to supply fuel cells or for applications such as the glass industry or the electronics industry. They may also be units intended for on-board use (trucks, boats, etc.).

The category of steam reforming processes for the production of hydrogen into which the present invention falls in particular employs an ethanol termed "denatured", which comprises a certain percentage of sulphur because such denaturing is generally carried out by adding a small quantity of gasoline containing sulphur. However, even at very low concentrations of the order of ten ppm, that sulphur constitutes a poison for the catalyst used in the steam reforming reactor. However, it can readily be extended to other types of feeds such as gasolines or gas oils which, after intense catalytic hydrotreatment, still contain some traces of sulphur-containing compounds, essentially of the thiophene, benzothiophene or dibenzothiophene type.

The steam reforming reactor is thus preceded by a reactor known as a guard reactor which can eliminate the sulphur-containing impurities contained in the denatured ethanol feed by adsorption onto an adsorbent solid.

The adsorbent solids which may be used in the guard reactor are generally of the nickel on alumina type (such as, for example, the adsorbent solid AxTrap-405 or D-1275, as sold in particular by Axens).

In their active phase (nickel primarily in the reduced state), they are known to be pyrophoric. Thus, they can only be handled in the open air if they have been passivated, for example with $CO_2$, which has to be removed to reactivate them prior to use in desulphurization. This activation may be carried out in the gas phase, in an inert gas such as nitrogen, or in a reducing atmosphere in the presence of hydrogen, or in the liquid phase, preferably using a desulphurized feed. The temperature for carrying out this operation is preferably in the range 100° C. to 350° C., preferably in the range 150° C. to 200° C.

The reactor for carrying out desulphurization of the steam reforming feed must therefore be activated by a phase for depassivation of the adsorbent solid which will then release $CO_2$ and render said adsorbent solid active.

The aim of the present invention is to essentially find a solution to this phase for activation of the guard reactor (or reactor for desulphurization of the steam reforming feed), while preventing the steam reforming reactor itself from being polluted by the sulphur.

EXAMINATION OF THE PRIOR ART

In the prior art, activation of the adsorbent solid is carried out using a stream of inert gas (for example nitrogen) which does not contain sulphur and is heated, for example to between 100° C. and 250° C., and typically between 150° C. and 200° C. This stream of gas must be maintained for a relatively long time (4 to 24 hours) and at high flow rates (between 200 and 500 $Nm^3/h/m^3$ of adsorbent).

Thus, this type of operation can only be envisaged if the gas serving for activation is available in sufficient quantities, which is not always the case. In addition, this solution is expensive because of the pure gas which is consumed.

In the prior art, a second alternative consisted of pre-activating the adsorbent and charging it in a neutral atmosphere (nitrogen), but that type of intervention is complex: a pressure suit is required, personnel have to be highly specialized, and expensive specific equipment is used, which is not always available. That type of operation is difficult and expensive to carry out, in particular for large units (when the volume of adsorbent exceeds a $m^3$).

A third alternative consists of supplying the reactor containing the guard bed which is ready for use, but that solution requires the transport of equipment which may be very heavy and bulky; several hundred liters or even several cubic meters.

Further, that solution means that a second reactor is required for switching with the first reactor when that first reactor is saturated with sulphur. In that alternative, a set of valves is necessary in order to isolate then remove the reactor containing said guard bed with a valve at the inlet and one at the outlet to keep it sealed. That solution is not economic, however, since the two reactors employed are too bulky and heavy (more than several tonnes).

BRIEF DESCRIPTION OF THE INVENTION

Figure 1:
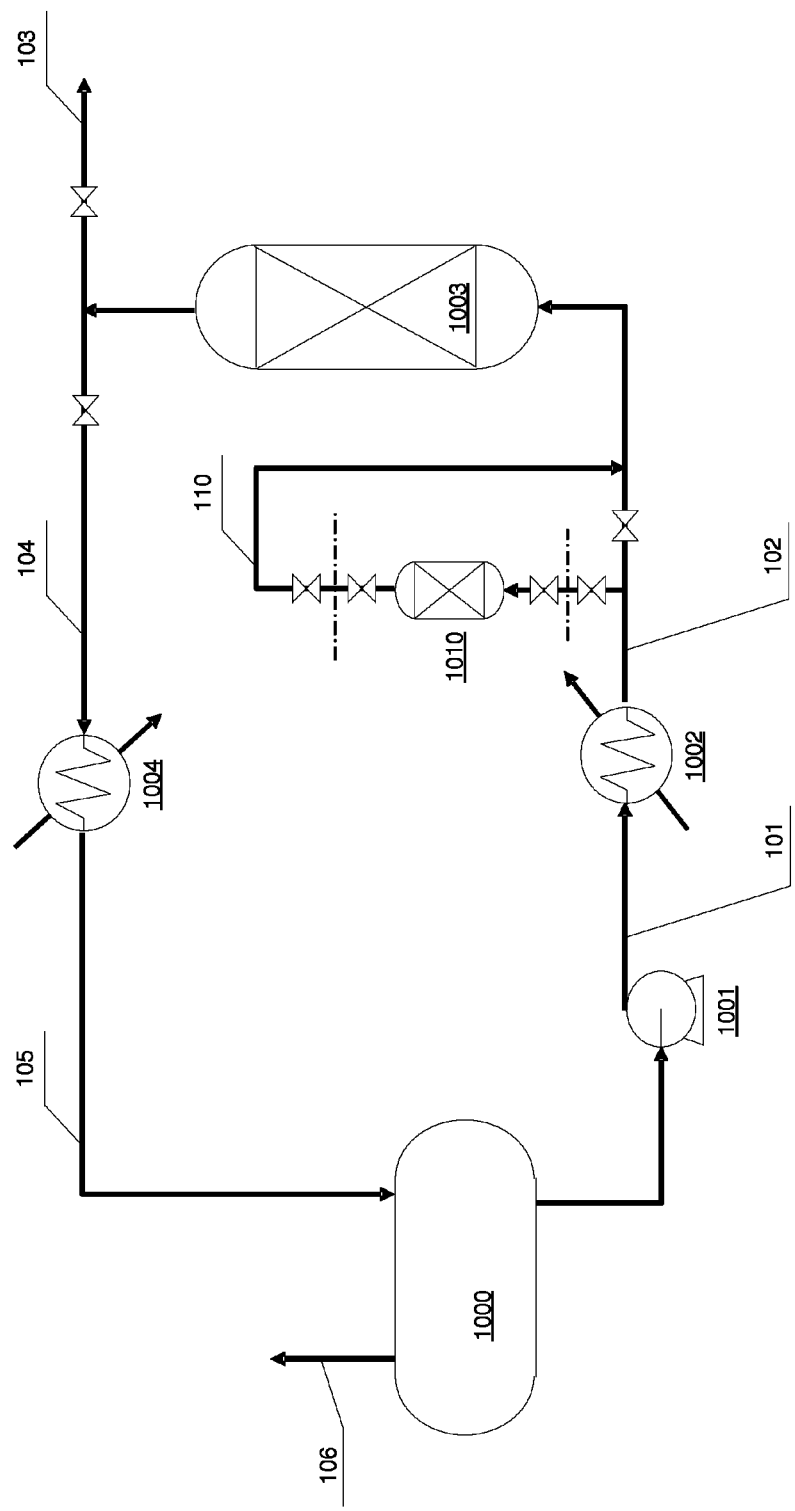
FIG. 1 represents a layout of a steam reforming feed preparation process in accordance with the present invention in the first variation in which the temporary desulphurization reactor and the permanent desulphurization reactor are in series.

The present invention can be defined as a process for pre-treating a steam reforming feed containing sulphur-containing compounds. This feed has to be desulphurized to less than 1 ppm in order to allow the steam reforming reactor to operate properly.

In the context of the present invention, the hydrocarbonaceous feed used as a steam reforming feed is generally denatured ethanol containing less than 10 ppm of sulphur.

The feed may also be a gasoline or gas oil type hydrocarbon feed containing less than 10 ppm of sulphur.

The steam reforming reactor is thus preceded by a desulphurization reactor which we shall hereinafter term the permanent desulphurization reactor.

The problem solved by the present invention is linked to the fact that the adsorbent solid allowing desulphurization in the permanent desulphurization reactor is delivered in a "passivated" state; in order to render it active, it has to be depassivated by thermal heating.

The solution developed by the present invention consists of using the steam reforming feed itself as a heat vector to allow depassivation of the adsorbent solid contained in the permanent desulphurization reactor.

However, this feed is initially charged with sulphur, and so it has to be desulphurized in a prior desulphurization reactor placed upstream of the permanent desulphurization reactor, which we term the temporary desulphurization reactor. The permanent desulphurization reactor is sometimes also known as the principal desulphurization reactor.

In the remainder of the text, the terms "pre-treatment reactor" and "desulphurization reactor" are strictly synonymous, since the pre-treatment in question consists of desulphurization.

Thus, the present invention can be defined as a process for pre-treating a steam reforming feed containing sulphur-containing compounds by adsorption of said sulphur-containing compounds onto an adsorbent solid, using two desulphurization reactors:
- a temporary desulphurization reactor containing an active adsorbent solid;
- a permanent desulphurization reactor placed upstream of the steam reforming unit, which contains an adsorbent solid in the passivated state, necessitating a depassivation phase in order to be rendered active;

the temporary desulphurization reactor being disconnected as soon as the adsorbent solid of the permanent desulphurization reactor has been activated, and the volume of the temporary desulphurization reactor being in the range 1/20 to 1/200 times the volume of the permanent desulphurization reactor, preferably in the range 1/50 to 1/200 of the volume of said permanent desulphurization reactor.

In a first variation of the process for pre-treating a steam reforming feed in accordance with the invention, said process comprises two phases:
- in the first phase, termed the activation phase, the steam reforming feed is sent to the temporary desulphurization reactor (1010) containing an active adsorbent solid, then to the permanent desulphurization reactor (1003) placed upstream of the steam reforming unit, the period of operation of the temporary desulphurization reactor (1010) being such that it allows the permanent desulphurization reactor (1003) to be activated by depassivation of the adsorbent solid contained in said reactor;
- in the second phase, the temporary desulphurization reactor (1010) is disconnected and the steam reforming feed is sent directly to the activated permanent desulphurization reactor (1003).

In a second variation of the process for pre-treating a steam reforming feed in accordance with the invention, said process comprises three phases:
- in the first phase, the steam reforming feed is sent to the temporary desulphurization reactor (1010) and the desulphurized feed obtained from said reactor is stored in a drum (1011);
- in the second phase, the desulphurized feed contained in the storage drum (1011) is heated in the exchanger (1002) then sent to the permanent pre-treatment reactor (1003), then is cooled in the exchanger (1004) at the outlet from the reactor (1003) before returning to the storage drum (1011), and said rotation from the storage drum (1011) to the permanent pre-treatment reactor (1003) is carried out until the latter has been activated;
- in the third phase, the temporary desulphurization reactor (1010) is disconnected and the steam reforming feed is sent directly to the activated permanent desulphurization reactor (1003).

The adsorbent solid used in the temporary desulphurization reactor and the permanent desulphurization reactor is usually constituted by nickel or a mixture of nickel and nickel oxide deposited on a support constituted by silica or silica-alumina.

The steam reforming feed is generally denatured ethanol containing less than 10 ppm of sulphur.

The steam reforming feed may also be a gasoline or gas oil type hydrocarbon feed containing less than 10 ppm of sulphur.

DETAILED DESCRIPTION OF THE INVENTION

The process for the pre-treatment of a hydrocarbon or ethanol feed for supplying a steam reforming unit in accordance with the invention consists of using the steam reforming feed itself as a stream for activation of the adsorbent solid contained in the permanent desulphurization reactor placed upstream of the steam reforming unit.

This permanent desulphurization reactor placed upstream of the steam reforming unit is vital in treating steam reformed feeds, whether they be denatured ethanol, gasoline or gas oil, which may contain up to 10 ppm of sulphur.

The permanent desulphurization reactor is designated in this way in order to distinguish it from the temporary desulphurization reactor which is only used in the present process to activate the adsorbent solid contained in the permanent desulphurization reactor.

Since the steam reforming feed contains sulphur, a temporary desulphurization reactor (1010) is placed upstream of the principal desulphurization reactor (1003).

This temporary desulphurization reactor (1010) typically has a volume 20 to 200 times smaller than that of the permanent desulphurization reactor (1003). Preferably, the volume of the temporary desulphurization reactor is 50 to 200 times smaller than the volume of principal desulphurization reactor (1003).

The temporary desulphurization reactor (1010) contains a directly active adsorbent solid and can be used to desulphurize a certain quantity of steam reforming feed over a relatively short period.

Thus, it is possible to have available a quantity of sulphur-free steam reforming feed for the 4 to 24 hours required, for example, for activation of the adsorbent solid contained in the permanent desulphurization reactor (1003).

In FIG. 1, which represents a first variation of the process of the invention, a set of valves means that the feed can pass through the temporary desulphurization reactor (1010) via the line (110).

As an example, in order to obtain an idea of the orders of magnitude, for a hydrogen production unit producing 100 $Nm^3/h$ of hydrogen from denatured ethanol (EtOH) containing 7 ppm of sulphur, the permanent desulphurization reactor (1003) will contain 900 liters of adsorbent solid in order to allow the steam reforming unit to operate for one year before replacing said adsorbent solid.

In this case, the temporary desulphurization reactor (1010) placed upstream of the permanent desulphurization reactor (1003) contains only approximately 5 liters of adsorbent solid to permit desulphurization of the steam reforming feed during the phase for activation of the adsorbent of said permanent desulphurization reactor (1003).

The temporary desulphurization reactor (1010) is advantageously equipped with an electrical heating means so that it can be readily isolated and even taken apart when activation of the adsorbent for the permanent desulphurization reactor (1003) is terminated.

In accordance with the invention, a line (104) for recycling the feed supplies a chiller (1004).

At the outlet from the chiller (1004), the feed which acted to activate the adsorbent solid returns, at ambient temperature, via the line (105) to the feed drum (1000) where it is separated from gases which will leave the feed drum (1000) via the outlet line (106).

These gases are discharged into the atmosphere as they are or, preferably, following treatment which is a function of the type of feed and the site under consideration.

According to the invention, the desulphurized feed acting to activate the adsorbent solid contained in the permanent desulphurization reactor can be sent directly to the reforming reactor via the line (103), rather than being recycled to the drum (1000) via the line (104).

After the phase for activation of the adsorbent solid of the permanent desulphurization reactor (1003), the stream of feed from the drum (1000) can be directed to the steam reforming unit by closing the line (104) with the aid of a valve and opening the valve for the line (103).

The temporary desulphurization reactor (1010) can easily be detached from the facility because it is small in size, or even be re-used in another facility once the pre-activated adsorbent solid has been replaced under a controlled atmosphere in the workshop.

The major advantage of the solution of the present invention is to reduce the costs of commissioning the adsorbent solid of the permanent desulphurization reactor (1003) without significantly increasing the investment costs.

Figure 2:
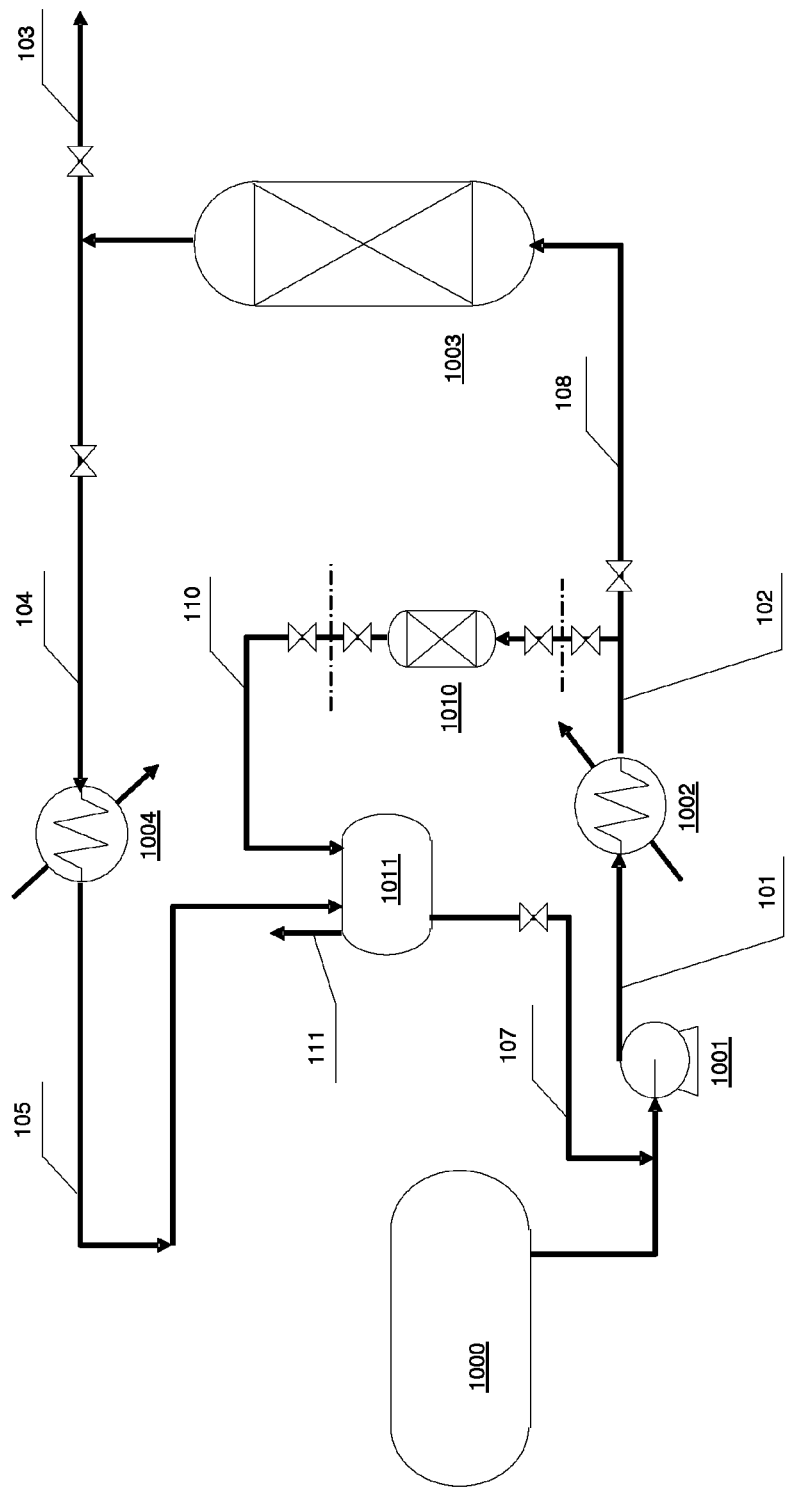
FIG. 2 represents a layout of a steam reforming feed preparation process in accordance with the present invention in the second variation in which the temporary desulphurization reactor operates on a bypass circuit on the normal circuit.

The variation of the invention shown in FIG. 2 consists of producing a reduced volume of purified steam reforming feed and shows, for example, only a few elements of the permanent desulphurization reactor (1003), treating the denatured ethanol on the temporary desulphurization reactor (1010).

This volume of purified ethanol can then be used in a closed loop to activate the adsorbent of the permanent desulphurization reactor (1003).

Compared with the preceding configuration, the size of the temporary desulphurization reactor (1010) containing the "pre-activated" adsorbent can be reduced by an order of magnitude.

A small volume of sulphur-containing hydrocarbon feed is sent from the drum (1000) through the temporary desulphurization reactor (1010) via the pump (1001) and the exchanger (1002) to be purified therein.

The purified feed is then stored in the small drum (1011) provided with a vent line (111). In order to activate the principal guard bed (1003), the purified feed is sent in a loop from the small drum (1011) towards the permanent desulphurization reactor (1003) via the line (107), the pump (1001), the exchanger (1002) and the line (108).

During the activation phase, the hydrocarbon feed which leaves the permanent desulphurization reactor (1003) is then returned to the small drum (1011) via the exchanger (1004) and the lines (104) and (105).

When the activation step is terminated, the sulphur-containing feed contained in the principal drum (1000) is sent to the permanent desulphurizaton reactor (1003) via the pump (1001), the exchanger (1002) and the line (108).

The purified feed leaving the permanent desulphurization reactor (1003) is then sent to the downstream steam reforming unit via the line (103).

EXAMPLES OF THE INVENTION

Basic case: Hydrogen was to be produced at a flow rate of 50 $Nm^3/h$ for a period of 8000 h (11 months) from denatured ethanol containing 2.5 ppm of sulphur-containing compounds.

Under the operating conditions of the steam reforming unit, the flow rate of ethanol required was 32 kg/h, i.e. approximately 40 L/h.

In order to remove the sulphur-containing compounds from the ethanol, essentially in the form of thiophene, Axen's solid AxTrap-405 was used in a fixed bed in the permanent desulphurization reactor operating at a temperature of 150° C. into which the denatured ethanol to be purified was passed.

Under the temperature and sulphur content conditions, the adsorption capacity of the solid for sulphur-containing compounds was 0.5 ppm (by weight).

The volume of ethanol to be treated was 322 $m^3$, which represented a mass of sulphur to be removed of 0.666 kg.

The mass of the AxTrap-405 solid to be used to carry out this operation was 129 kg, i.e. a volume of 161 L.

This solid had been activated in the liquid phase using 12 $m^3$ of purified ethanol containing no sulphur, at a temperature of 150° C., for 8 h. This volume represented approximately 75 times the volume of the permanent desulphurization reactor. This volume of 12 $m^3$ of purified ethanol (no sulphur) represents a quantity of ethanol that is difficult to obtain in view of legislation which applies beyond a certain used volume of denatured ethanol (very probably containing sulphur) which cannot be used as such to activate the permanent desulphurization bed in an optimized manner.

Example 1, in Accordance with the Invention

In this example, the pure ethanol necessary for activation of the permanent desulphurization reactor was produced by treating the denatured ethanol on a temporary desulphurization reactor containing solid AxTrap-405 already activated ex-situ and ready for use.

The volume of pure ethanol necessary to activate the permanent desulphurization reactor at 150° C. was still 12 $m^3$, which represented a quantity of sulphur of 0.024 kg, and required a mass of solid AxTrap-405 of 4.8 kg, i.e. a volume of 6 L.

The volume of the temporary desulphurization reactor (6 L) was equal to approximately 4% of that of the volume of the permanent desulphurization reactor.

Example 2, in Accordance with the Invention

In this example, the pure ethanol necessary for activation of the permanent desulphurization reactor was produced by treating the denatured ethanol on a temporary desulphurization reactor containing solid AxTrap-405 already activated ex-situ and ready for use.

The pure ethanol produced in this manner was used in a loop, which meant that the necessary volume could be reduced and thus the volume of denatured ethanol to be purified via the temporary desulphurization reactor could be reduced and as a result, the volume of said temporary desulphurization reactor could be reduced.

A volume of purified ethanol equal to 10 times the volume of the principal desulphurization reactor was used, i.e.

approximately 1.6 m³, which was used in a loop by recirculating it in order to activate the principal desulphurization reactor.

This volume of ethanol of 1.6 m³ contained 0.003 kg of sulphur, which required the use of 0.6 kg of solid AxTrap-405, i.e. a volume of approximately 0.8 L.

The volume of the temporary desulphurization reactor was equal to approximately 0.5% of the volume of the permanent desulphurization reactor. This variation meant that the volume of the temporary desulphurization reactor as well as the volume of denatured ethanol that had to be purified on this temporary reactor and which was used to activate the permanent desulphurization reactor could be considerably reduced.

The invention claimed is:

1. A process for pre-treating a steam reforming feed containing sulphur-containing compounds, said process comprising:
   adsorption of said sulphur-containing compounds onto an adsorbent solid, using two desulphurization reactors:
   a temporary desulphurization reactor containing an active adsorbent solid;
   a permanent desulphurization reactor placed upstream of a steam reforming unit, which contains an adsorbent solid in the passivated state, necessitating a depassivation phase in order to be rendered active;
   wherein said temporary desulphurization reactor is disconnected as soon as the adsorbent solid of the permanent desulphurization reactor has been activated, and
   wherein the volume of said temporary desulphurization reactor is in the range of 1/20 to 1/200 times the volume of said permanent desulphurization reactor.

2. The process according to claim 1, wherein said process comprises a first phase and a second phase:
   wherein in said first phase, termed the activation phase, said steam reforming feed is sent to said temporary desulphurization reactor (1010) containing an active adsorbent solid, and then to said permanent desulphurization reactor (1003) placed upstream of the steam reforming unit, and wherein the period of operation of said temporary desulphurization reactor (1010) is such that it allows said permanent desulphurization reactor (1003) to be activated by depassivation of said adsorbent solid contained in said permanent desulphurization reactor; and
   wherein in said second phase, said temporary desulphurization reactor (1010) is disconnected and said steam reforming feed is sent directly to said activated permanent desulphurization reactor (1003).

3. The process according to claim 1, wherein said process comprises a first phase, a second phase, and a third phase:
   wherein in said first phase, said steam reforming feed is sent to said temporary desulphurization reactor (1010) and the desulphurized feed obtained from said temporary desulphurization reactor is stored in a drum (1011);
   wherein in said second phase, said desulphurized feed contained in said storage drum (1011) is heated in a exchanger (1002), then sent to said permanent pre-treatment reactor (1003), and then cooled in a exchanger (1004) at the outlet from said permanent pre-treatment reactor (1003) before returning to said storage drum (1011), and the flow of desulphurized feed from storage drum (1011) to the permanent pre-treatment reactor (1003) and return to said storage drum (1011) is carried out until said permanent pre-treatment reactor (1003) latter has been activated; and
   wherein in said third phase, said temporary desulphurization reactor (1010) is disconnected and said steam reforming feed is sent directly to the activated permanent desulphurization reactor (1003).

4. The process according to claim 1, wherein said adsorbent solid used in said temporary desulphurization reactor and said permanent desulphurization reactor contains nickel or a mixture of nickel and nickel oxide deposited on a silica or silica-alumina support.

5. The process according to claim 1, wherein said steam reforming feed is denatured ethanol containing less than 10 ppm of sulphur.

6. The process according to claim 1, wherein said steam reforming feed is a gasoline or a gas oil containing less than 10 ppm of sulphur.

7. The process according to claim 1, wherein the volume of said temporary desulphurization reactor is in the range of 1/50 to 1/200 times the volume of said permanent desulphurization reactor.

* * * * *